US006066589A

United States Patent [19]
Malentacchi et al.

[11] Patent Number: 6,066,589
[45] Date of Patent: May 23, 2000

[54] HYDROGENATION CATALYSTS

[75] Inventors: Marinella Malentacchi, Castiglion Fiorentino; Luigi Cavalli, Novara; Carlo Rubini, San Fermo Della Battaglia, all of Italy

[73] Assignee: Sud Chemie MT. S.r.l., Milan, Italy

[21] Appl. No.: 09/081,335

[22] Filed: May 19, 1998

[51] Int. Cl.[7] .................................................... B01J 21/18
[52] U.S. Cl. ............................ 502/185; 502/180; 502/182; 502/184
[58] Field of Search ..................................... 502/185, 180, 502/182, 184

[56] References Cited

U.S. PATENT DOCUMENTS

| | | |
|---|---|---|
| 3,138,560 | 6/1964 | Keith et al. . |
| 4,093,559 | 6/1978 | Fernholz et al. . |
| 4,421,676 | 12/1983 | Puskas et al. . |
| 4,467,111 | 8/1984 | Puskas et al. . |
| 4,476,242 | 10/1984 | Puskas et al. . |
| 5,614,001 | 3/1997 | Kosaka et al. ............................ 96/10 |

FOREIGN PATENT DOCUMENTS

WO 93/18856   of 1993   WIPO .

OTHER PUBLICATIONS

Hungarian Abstract of HU 179197 (1981), no month available.

Hungarian Abstract of HU 203685 (1990), no month available.

Hungarian Abstract of HU 176211 (1981), no month available.

Derwent English language abstract of HU 203685 (1990), no month available.

Search report issued in connection with Hungarian counterpart application, no date available.

Krishnankutty, N., et al. ,"The Effect of pretreatment of Pd/C Catalysts, 1. Adsorption and Absorption Properties." *Journal of Catalysts*, vol. 155, No. 2: pp. 312–326 (1995), no year available.

English language abstract of International Application Publication No. WO 93/18856, no date available.

*Primary Examiner*—Elizabeth D. Wood
*Attorney, Agent, or Firm*—Bryan Cave LLP

[57] ABSTRACT

Hydrogenation catalysts comprising metallic palladium supported on activated carbon, wherein less than 50% by weight of the palladium is comprised within a surface layer with a depth of up to 50 microns, the remainder being comprised in a layer between 50 and 400 microns deep. The catalysts can be used in particular in purifying terephthalic acid obtained by oxidation of p-xylene.

15 Claims, No Drawings

HYDROGENATION CATALYSTS

The present invention relates to hydrogenation catalysts which comprise palladium supported on activated carbon, their method of preparation and their use in hydrogenation reactions.

In particular, it relates to the use of catalysts in the purification of terephthalic acid from impurities comprising 4-carboxybenzaldehyde (4-CBA).

Hydrogenation catalysts comprising palladium supported on activated carbon are known in the literature. They are prepared by adsorbing a palladium compound on activated carbon and by then reducing the adsorbed compound to palladium metal.

BACKGROUND OF THE INVENTION

It is known, from U.S. Pat. No. 3,138,560, that if the palladium is adsorbed from a solution of sodium tetrachloropalladate or palladium chloride, most of the palladium is reduced immediately and deposited on the surface in the form of a thin film of palladium metal.

The resulting catalysts are scarcely active. Reduction of palladium to metallic palladium is attributed to functional groups, such as the aldehyde groups that are present on the surface of the activated carbon.

In order to avoid this reduction, palladium compound solutions have been used which contain an oxidizing agent, such as hydrogen peroxide.

In order to be able to deposit on the surface of the activated carbon palladium crystallites having a relatively small size (smaller than 35 Å if possible), solutions of the palladium compound in organic solvents have been used (U.S. Pat. No. 4,476,242). In this case, all of the palladium is concentrated in a layer less than 70–80 microns thick.

Results similar to those mentioned above are achieved if the palladium is deposited from aqueous solutions of sodium tetranitropalladate (U.S. Pat. No. 4,421,676).

According to conventional methods, the catalyst is prepared by washing the activated carbon with water in order to eliminate the fines; the carbon thus treated is dispersed in water, optionally correcting its basicity, and the aqueous solution of the palladium salt is then added thereto drop by drop.

The impurities contained in the terephthalic acid obtained by oxidation of p-xylene are consist primarily of paratoluic acid and 4-CBA.

Whilst paratoluic acid can be removed by cooling and crystallization of the terephthalic acid solutions that contain it, removal of 4-CBA requires transformation by reduction to compounds which can be separated by crystallization.

The transformation is performed by hydrogenation on palladium catalysts on an activated carbon support.

The catalysts must have high activity and selectivity in order to reduce the concentration of 4-CBA to levels acceptable to users of terephthalic acid and to convert said 4-CBA into compounds that can be separated by crystallization.

SUMMARY OF THE INVENTION

It has been unexpectedly found that the activity and selectivity of catalysts that comprise palladium supported on activated carbon can be improved considerably if the palladium compound is dry-impregnated on the activated carbon, adsorbing the palladium compound preferably from concentrated aqueous solutions which are used in an amount equal to, or lower than, the volume of the pores of the activated carbon.

DETAILED DESCRIPTION OF THE INVENTION

Preferably, the support is impregnated by spraying the palladium compound solution on the activated carbon, preferably by using amounts of solution equal to ½ to ⅕ of the volume of the carbon pores (pore volume is determined by multiplying the weight of the activated carbon used for supporting by the porosity of the carbon).

Operating according to this method, less than 50% of the palladium metal is comprised in a layer up to 50 microns deep; the remainder is comprised in a layer from 50 to 400 microns depth.

Distribution of the palladium is determined by X-ray electron microprobe analysis (EMPA).

The palladium compounds that can be used are of various kinds. Examples are halides, diacetate, nitrate, alkaline salts of chloropalladium acid, complexes of Pd with amines, and salts such as sodium tetranitropalladate ($Na_2 Pd (NO_2)_4$).

Preferably, compounds are used which are highly soluble in water, such as sodium tetrachloropalladate. In this case, the palladium salt is used at concentrations equal to 1–10% by weight.

In other cases, the concentration of the palladium compound is preferably equal to 50–100% of its saturation concentration measured at room temperature.

The solution of the palladium compound is sprayed, using devices of known type, at a rate of 0.1–1 ml of solution per minute per 100 g of support.

The spraying is preferably carried out at room temperature. If the temperature increases, the drying rate increases, possibly forming a very fine disperse phase; however, the rate of spontaneous reduction of palladium also increases, possibly forming an undesirable thin film of palladium metal on the surface of the support.

After spraying, the support impregnated with the palladium compound solution, in which support the palladium can be already partly in the state of palladium metal, is treated with reducing agents of a known kind, used to reduce palladium to metallic palladium, in order to complete palladium reduction.

It is possible to use compounds such as formaldehyde, sodium hypophosphite, glucose and others. It is also possible to use hydrogen, provided that the reduction is performed at room temperature or slightly above it (the use of high temperatures leads to an undesirable size increase of the crystallites).

Very conveniently, a solution of hypophosphite at 8–10% concentration is used, using a volume of solution which is smaller than the pore volume. The catalyst is then drained from the solution, washed and dried.

The activated carbon used to prepare the catalysts can be of animal origin or plant origin. Coconut carbon is preferred. The surface area of the carbon is preferably greater than 600 $m^2/g$ (BET) and can reach 1000 $m^2/g$ or more; the porosity (BET) is from 0.3 to 0.9 $cm^3/g$. The carbon is preferably used in granular form, with a particle size generally between 2 and 15 mesh; however, it is possible to use activated carbon in the form of flakes, pellets or other granular forms.

The fine fraction of the carbon (fines) is eliminated in a dry air stream and/or by screening.

The activated carbon is preferably pretreated, before spraying the solution of the Pd compound, with an acidified aqueous solution which contains for example 1–5% by weight of concentrated HCl. The solution is sprayed on the activated carbon in an amount which is equal to, or smaller than, the pore volume.

The treatment with the acid solution improves the activity of the catalyst.

The amount of Pd fixed on the activated carbon is generally from 0.1 to 5% by weight; preferably, in the case of catalysts for purifying terephthalic acid, from 0.2 to 0.6% by weight; more preferably, from 0.3 to 0.5% by weight. In addition to palladium, other metals, such as rhodium or copper, may be present. Purification of crude terephthalic acid using the catalysts of the invention is performed by heating a suspension of said acid in water, working at temperatures between approximately 100° and 300° C. and with a hydrogen pressure of approximately 15 to 100 bar.

The catalysts can also be used to purify potable water from nitrate and/or nitrite ions and organic chlorides (e.g. trichloroethylene). In this case, the catalysts, in addition to palladium, preferably also comprise copper with a Pd/Cu ratio from 2:1 to 20:1.

In the case of nitrates, the process is carried out at room temperature, making the water and a stream of hydrogen flow through a fixed bed of the catalyst, whilst in the case of chlorides the process is conducted at between 15° and 150° C.

The palladium catalysts obtained with the method according to the invention are characterized by a distribution of palladium metal crystallites on the surface of the activated carbon granules such that less than 50% of the palladium is comprised within a 50-micron layer and the remainder is distributed from a depth of 50 to 400 microns.

The surface area of the palladium crystallites, referred to palladium metal, is greater than 150 $m^2/g$ palladium and can be as high as 300 $m^2/g$ or more; with reference to the catalyst, the surface area is higher than 0.8 $m^2/g$ and can reach 1.5–2 $m^2/g$.

The surface area referred to the palladium is obtained from the CO chemisorption data; the surface area relative to the catalyst is obtained by BET determination.

The average numerical longitudinal size of the crystallites is generally lower than 100 AÅ: in some cases it can decrease (particularly in catalysts obtained by spraying) to values of less than 50 AÅ or even less than 35 AÅ (35 AÅ is the limit below which it is not possible to determine the dimensions of the crystallites by X-ray measurements). The average size of the crystallites is determined from X-ray diffraction data). The percentage of crystallites with average size of less than 35 AÅ is determined by calculating the difference between the concentration of Pd on the catalyst (which is determined by chemical methods) and the concentration that results from the percentage of crystallites with size greater than 35 AÅ.

The catalysts of the invention are furthermore characterized by CO chemisorption values, referred to the catalyst, of more than 0.2 ml CO/g catalyst and which can arrive up to 0.5 ml CO/g cat; the chemisorption referred to the palladium is higher than 50 ml/g Pd and can reach 100 ml/g Pd.

CO chemisorption is measured by feeding known volumes of CO to the sample.

These feeds are performed until the sample, saturated with CO, is no longer able to chemisorb and releases constant volumes of CO corresponding to the fed volumes.

Measurements are performed at room temperature: approximately 6 g of dry catalyst are introduced in a U-shaped sample holder provided with an inlet valve and with an outlet valve.

Before analysis, the sample is treated with hydrogen at room temperature so as to reduce the Pd that may have oxidized during sample drying and to also eliminate any trace of oxygen, which would entail conversion of CO to $CO_2$.

The sample is then flushed with helium in order to eliminate any trace of hydrogen.

Known volumes of CO (measured with a loop set to a known volume) are then fed in a stream of inert gas (helium): the adsorbed volumes are measured with a heat conductivity cell.

The chromatogram related to chemisorption has various peaks: each peak relates to a feed of CO to the sample.

Catalytic activity (measured according to a standard 4-CBA hydrogenation test and expressed as slope of the line obtained by plotting the logarithm of the concentration of 4-CBA as a function of the reaction time in minutes) is higher than 0.05 and can reach 0.08. Activity, expressed as the ratio of the slope to the weight of Pd in grams, is higher than 10 and can reach 20. Conversion of 4-CBA after 45 minutes of reaction is higher than 90% and can reach 99%.

The hydrogenation reaction is performed in a 2-liter autoclave equipped with a blade stirrer and with a wire-mesh catalyst holder.

An automatic valve allows immersion of the holder in the reaction solution only when the reaction conditions are reached (200° C.). The autoclave has a riser from which samples can be taken at regular intervals. 1.5 l of aqueous solution containing 500 ppm of 4-CBA are introduced in the autoclave and 0.750 g of catalyst are loaded into the catalyst holder in a raised position.

The autoclave is closed and washed first with argon, in order to eliminate all traces of oxygen, and then with nitrogen. 18 bar of hydrogen are then loaded before commencing agitation and heating.

Once the operating temperature (200° C.) has been reached, but before immersing the holder in the solution, a sample is taken which constitutes the time-zero sample.

Successive samples are then taken at preset times (5, 10, 15, 20, 30, 45, 60 and 90 minutes). All the samples are analyzed by HPLC in order to determine the content of residual 4-CBA and hydroxymethylbenzoic acid and paratoluic acid that have formed.

In addition to having high activity, the catalysts according to the invention are also characterized by considerable selectivity in the reduction of 4-CBA to paratoluic acid and hydroxymethylbenzoic acid (by way of example, after operating for 45 minutes according to the above described test, 200 to 300 ppm of the above mentioned acids form).

By using a catalyst of known type, obtained for example according to U.S. Pat. No. 4,476,242, and by operating according to the above described test, slopes of less than 0.04 are obtained for the lines that plot the logarithm of 4-CBA concentration as a function of time in minutes. The concentration of paratoluic acid and p-hydroxymethylbenzoic acid is lower than 100 ppm.

The following examples are given to illustrate but not to limit the invention.

EXAMPLE 1

500 g of coconut charcoal in flakes, with a surface area (BET) of 1100 $m^2/g$, a porosity (BET) of 0.68 $cm^3/g$ and a particle size between 4 and 8 mesh, and from which the fines have been eliminated by moderate screening and flushing with nitrogen, were loaded into a jar equipped with a motor speedvariator which allowed said jar to rotate (24 rpm).

40 ml of an aqueous solution containing 7.1 g of $Na_2PdCl_4$, brought to a pH between 0 and 1 with HCl and with the addition of 6 ml of $H_2O_2$ in an amount equal to 35% by weight, were sprayed over 20 minutes onto the carbon, which was rotated continuously.

Impregnation was performed at room temperature while the jar was rotating.

At the end of the spraying process, the activated carbon, which maintained its original appearance, was treated with 300 ml of an aqueous solution containing 25 g of $NaH_2PO_2 \cdot H_2O$.

The catalyst was drained, washed and dried at 120° C.

The palladium content was 0.413% by weight.

The other characteristics of the catalyst and its activity in reducing 4-CBA according to the above described standard test are presented in the table.

EXAMPLE 2

The preparation of Example 1 was repeated, except that the carbon impregnation was performed by adding, in the jar, 300 ml of the sodium chloropalladate solution.

The content of Pd in the finished catalyst was 0.464% by weight.

The characteristics of the catalyst and its activity are presented in the table.

COMPARATIVE EXAMPLE 1

The test of Example 2 was repeated, except that the carbon was flushed with water in order to eliminate the fines and then impregnated with 600 ml of solution of the Pd salt. 5 minutes after the addition, the solution was colorless and the support had a metallic appearance.

Reduction was completed by adding 50 ml of aqueous solution containing 25 g of sodium hypophosphite.

The Pd content in the finished catalyst was 0.474% by weight.

Other characteristics of the catalyst and its activity according to the standard test are presented in the table.

EXAMPLE 3

The preparation of Example 1 was repeated, the only difference being that the activated carbon from which the fines had been eliminated, as in Example 1, was pretreated with an aqueous solution of HCl before impregnation with the palladium salt solution. Pretreatment with the HCl solution was performed with the same method used for impregnation, that is to say, by spraying the HCl solution (100 ml containing 3.5% by weight of HCl) onto the carbon contained in the jar which rotates continuously.

The characteristics of the catalyst are presented in the table.

X-ray electron microprobe analysis was conducted on the fractures of some granules of the catalyst. This method (EMPA) consists in detecting the primary X-ray radiation, which is typical of an element, in a sample subjected to electron bombardment.

Using the EDX (or EDS, energy dispersive spectrometer) method, it is possible to quickly evaluate the elements that constitute the sample being examined and to obtain composition maps. However, the resolution of this system is too low (150 ev) to obtain reliable information on the concentration of the elements at issue.

In order to obtain quantitative information it is necessary to have higher resolutions, which are obtained by using the WDX (or WDS, wavelength dispersive spectrometer) method. In this case, one obtains distinctly higher resolutions (10 ev) and the quantitative charts that plot the percentage of Pd as a function of the position of the beam on the surface of the fracture have been obtained with this system.

In this case, full quantitative analysis along an axis of the scanning area is obtained point by point, by shifting the coordinates of the electron beam after each acquisition, with the aid of a computer.

The profile of the $L^{alpha}$ radiation of the palladium along a line that includes the entire thickness of the granule shows that the palladium is comprised within a layer which is approximately 350 microns deep and that less than 50% of the palladium is in a layer which is 50 microns deep.

EXAMPLES 4 AND 5

The preparation of Example 3 was repeated, the only difference being that in Example 4 a solution of 100 ml of 7% HCl by weight was sprayed and that in Example 5, 200 ml of a solution of 1.75% HCl by weight was sprayed.

The characteristics of the catalysts are presented in the table.

COMPARATIVE EXAMPLE 2

Catalyst prepared according to Example C of U.S. Pat. No. 4,476,241.

12 g of the activated carbon in flakes used in Example 1 are washed with methanol in order to remove the fines. The methanol was decanted and the carbon transferred into a 300-ml three-necked flask and then suspended in 40 ml of methanol. The dispersion system was agitated by immersing the vanes of the agitator in the upper layer of the liquid (without contact with the solid).

Cooling to 5° C. is performed and a solution of 0.072 g of Pd $(NO_3)_2$ in 50 ml of methanol is introduced drop by drop. Agitation was continued for 21 hours.

Water was then added and the catalyst was washed and dried at 60° C.

The Pd content on the catalyst was 0.17% by weight. The catalyst had a metallic appearance (indicating poor dispersion of the palladium).

The characteristics of the catalyst are presented in the table.

Electron microprobe analysis, as described in Example 3, indicated that all the palladium was comprised in a layer with a depth of 60 to 70 microns.

TABLE

| CAT Example | Pd % by weight | Chemiad. CO/g.cat. | Crystallites A° | Pd Area $m^2$/g Pd | Activity slope | Activity slope/g Pd | Conv. % of 4-CBA at 45' |
|---|---|---|---|---|---|---|---|
| Ex. 1 | 0.413 | 0.34 | 53 | 339 | 0.065 | 15.74 | 94.4 |
| Ex. 2 | 0.464 | 0.275 | 105 | 244 | — | — | — |
| Ex. 3 | 0.498 | 0.36 | 34 | 296 | 0.073 | 4.66 | 96.7 |
| Ex. 4 | 0.486 | 0.2 | 68 | 168 | 0.0572 | 11.77 | 92.9 |
| Ex. 5 | 0.485 | 0.31 | 44 | 264 | 0.0678 | 13.98 | 95.2 |
| Comp. Ex. 1 | 0.474 | 0.17 | 87 | 148 | 0.0409 | 8.63 | 84.9 |
| Comp. Ex. 2 | 0.17 | 0.04 | 76 | 97 | 0.0395 | 23.24 | 83.2 |

What is claimed is:

1. Hydrogenation catalysts comprising palladium metal supported on activated carbon, wherein the palladium is comprised within a surface layer up to 400 microns in depth and wherein less than 50% by weight of the palladium is located in the first 50 microns of the surface layer.

2. Catalysts according to claim 1, wherein the palladium is present in the form of crystallites having an average numerical longitudinal size of less than 100 Å, the catalyst being capable of chemisorbing carbon monoxide in an amount higher than 0.2 ml CO/g of catalyst.

3. Catalysts according to claim 2, wherein the values of the chemisorption of carbon monoxide are higher than 50 ml CO/g palladium fixed on the carbon.

4. Catalysts according to claim 1, wherein the palladium content is between 0.1 and 5% by weight.

5. Catalysts according to claim 2, wherein the palladium content is from 0.2 to 0.6% by weight.

6. Catalysts according to claim 2, wherein the palladium has a surface area between 150 and 300 $m^2/g$.

7. Catalysts according to claim 1, wherein the catalyst further comprises a metal selected from the group consisting of rhodium and copper.

8. Catalysts according to claim 2, wherein the average size of the palladium crystallites is less than 50 Å.

9. Catalysts according to claim 2, wherein the average size of the palladium crystallites is less than 35 Å.

10. Catalysts according to claim 1, wherein the activated carbon is coconut carbon and has a surface area of more than 600 $m^2/g$.

11. Method for preparing the catalysts according to claim 1, wherein an aqueous solution of a palladium compound is dry-impregnated on activated carbon, using an amount of solution which is equal to, or lower than, the pore volume of the carbon.

12. Method according to claim 11, wherein impregnation is carried out by spraying.

13. Method according to claim 11, wherein adsorption is carried out from solutions of the palladium compound at concentrations equal to 70–90% of the saturation concentration at room temperature.

14. Method according to claim 11, wherein the activated carbon is pretreated with acid solutions having a pH between 0 and 1, using amounts of solution which are equal to, or lower than, the pore volume of the carbon.

15. Catalysts according to claim 1, the catalyst being capable of chemisorbing monoxide in an amount higher than 0.2 ml CO/g of catalyst.

* * * * *

UNITED STATES PATENT AND TRADEMARK OFFICE
CERTIFICATE OF CORRECTION

PATENT NO : 6,066,589

DATED : May 23, 2000

INVENTOR(S) : Malentacchi, et al.

It is certified that error appears in the above-identified patent and that said Letters Patent are hereby corrected as shown below:

Column 3, lines 32, 34, 39, 43 and column 6, at the heading of column 4, "AÅ" should be --Å--.

Signed and Sealed this

Tenth Day of April, 2001

Attest:

NICHOLAS P. GODICI

Attesting Officer

Acting Director of the United States Patent and Trademark Office